(12) United States Patent
Takemoto

(10) Patent No.: US 9,808,584 B2
(45) Date of Patent: *Nov. 7, 2017

(54) ELASTIC CAP AND SYRINGE ASSEMBLY THEREWITH

(71) Applicant: TERUMO KABUSHIKI KAISHA, Tokyo (JP)

(72) Inventor: Masafumi Takemoto, Fujinomiya (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/353,438

(22) Filed: Nov. 16, 2016

(65) Prior Publication Data

US 2017/0056599 A1 Mar. 2, 2017

Related U.S. Application Data

(63) Continuation of application No. 14/641,019, filed on Mar. 6, 2015, now Pat. No. 9,545,485, which is a
(Continued)

(51) Int. Cl.
*A61M 5/32* (2006.01)
*A61M 5/34* (2006.01)
*A61M 5/31* (2006.01)

(52) U.S. Cl.
CPC ........ *A61M 5/3202* (2013.01); *A61M 5/3134* (2013.01); *A61M 5/343* (2013.01); *A61M 2205/0216* (2013.01)

(58) Field of Classification Search
CPC ........ A61M 5/3202; A61M 2205/0216; A61M 5/3134; A61M 5/343; A61M 5/3213
(Continued)

(56) References Cited

U.S. PATENT DOCUMENTS 4,474,734 A * 10/1984 Cooper .................. A61L 2/07
422/26
4,986,818 A * 1/1991 Imbert ................ A61M 5/3213
604/192
(Continued)

FOREIGN PATENT DOCUMENTS

DE  89 06 101 U1  6/1989
EP  0 229 204 A1  7/1987
(Continued)

OTHER PUBLICATIONS

International Search Report issued in International Patent Application No. PCT/JP2013/058827 dated Jul. 2, 2013.
(Continued)

*Primary Examiner* — Gerald Landry, II
(74) *Attorney, Agent, or Firm* — Foley & Lardner LLP

(57) ABSTRACT

An elastic cap detachably mountable to a barrel tip portion of a barrel so as to seal a tip of a needle hole includes a cylindrical receiving hole configured to receive at least part of a barrel tip portion and a puncture needle of a barrel. The receiving hole includes a first inner diameter portion having a smaller diameter than an outer diameter of the annular head; a stopper portion provided at an end of the first inner diameter portion; and a second inner diameter portion that is formed from the stopper portion to a bottom wall provided at an end of the second inner diameter portion, the second inner diameter portion having a smaller diameter than the first inner diameter portion.

16 Claims, 8 Drawing Sheets

Related U.S. Application Data continuation of application No. PCT/JP2013/058827, filed on Mar. 26, 2013.

(58) Field of Classification Search
USPC .......................... 604/162, 164.08, 192, 198
See application file for complete search history.

(56) References Cited

U.S. PATENT DOCUMENTS

| | | | |
|---|---|---|---|
| 5,085,647 A * | 2/1992 | Henderson | A61M 5/3213 604/192 |
| 5,254,099 A | 10/1993 | Kuracina et al. | |
| 5,746,733 A | 5/1998 | Capaccio et al. | |
| 5,980,495 A * | 11/1999 | Heinz | A61M 5/3202 128/919 |
| 6,017,325 A | 1/2000 | Yerfino et al. | |
| 6,551,286 B1 * | 4/2003 | Claessens | A61M 5/3202 128/919 |
| 6,719,732 B2 | 4/2004 | Courteix | |
| 7,559,919 B2 * | 7/2009 | Pech | A61M 5/3202 604/192 |
| 7,641,636 B2 * | 1/2010 | Moesli | A61M 5/3202 604/162 |
| 7,828,777 B2 | 11/2010 | Vetter et al. | |
| 2002/0045858 A1 | 4/2002 | Alchas et al. | |
| 2002/0062108 A1 | 5/2002 | Courteix | |
| 2003/0181859 A1 * | 9/2003 | Brunel | A61M 5/3202 604/192 |
| 2005/0038391 A1 * | 2/2005 | Wittland | A61L 2/20 604/192 |
| 2007/0156100 A1 * | 7/2007 | Moesli | A61M 5/3202 604/198 |
| 2008/0118678 A1 | 5/2008 | Huang et al. | |
| 2008/0269690 A1 * | 10/2008 | Felix-Faure | A61M 5/3202 604/192 |
| 2009/0030376 A1 | 1/2009 | Teufelberger et al. | |
| 2009/0118678 A1 * | 5/2009 | Kawashima | A61M 5/3213 604/197 |
| 2009/0192486 A1 | 7/2009 | Wilmot et al. | |
| 2009/0204026 A1 | 8/2009 | Crawford et al. | |
| 2010/0205511 A1 | 8/2010 | Murakami et al. | |
| 2010/0305511 A1 * | 12/2010 | Thibault | A61M 5/3202 604/192 |
| 2011/0040280 A1 | 2/2011 | Ijitsu et al. | |
| 2012/0215179 A1 | 8/2012 | Halili et al. | |
| 2013/0012886 A1 * | 1/2013 | Kawachi | A61M 5/3202 604/192 |
| 2016/0106929 A1 * | 4/2016 | Fournier | A61M 5/3204 604/192 |

FOREIGN PATENT DOCUMENTS

| | | |
|---|---|---|
| EP | 0 592 814 A2 | 4/1994 |
| JP | H10-305098 A | 11/1998 |
| WO | WO-2011/114917 A1 | 9/2011 |

OTHER PUBLICATIONS

English Translation of the Written Opinion of the International Searching Authority issued in International Patent Application No. PCT/JP2013/058827 dated Jul. 2, 2013.
Supplementary European Search Report and Search Opinion issued in European Patent Application No. 13880580.9 dated Oct. 17, 2016.
English Translation of Notification of Reasons for Refusal issued in Japanese Patent Application No. 2015-507746 dated Jan. 19, 2016.
English Translation of Decision of Refusal issued in Japanese Patent Application No. 2015-507746 dated Aug. 30, 2016.

\* cited by examiner

ELASTIC CAP AND SYRINGE ASSEMBLY THEREWITH

CROSS-REFERENCE TO RELATED APPLICATIONS

This application is a continuation of U.S. patent application Ser. No. 14/641,019, filed on Mar. 6, 2015, which is a continuation application filed under 35 U.S.C. 111(a) claiming the benefit under 35 U.S.C. §§120 and 365(c) of PCT International Application No. PCT/JP2013/058827, filed on Mar. 26, 2013, the contents of which are hereby incorporated by reference in their entireties.

BACKGROUND

Technical Field

The present disclosure relates to an elastic cap detachably mounted to the tip portion of a barrel from which a puncture needle projects and a syringe assembly with the elastic cap.

Background Art

For example, as shown in U.S. Pat. No. 6,719,732, a prefilled syringe in which a drug or the like is pre-filled is provided with an elastic cap detachably mounted to the tip portion of a barrel having a puncture needle, thereby protecting the puncture needle and sealing the needle hole of the puncture needle.

The elastic cap is attached before a plunger is inserted into the interior space of the barrel and before the barrel is filled with a drug or the like. The process of attaching the elastic cap to the barrel in accordance with the prior art is described below with reference to FIGS. 4 and 5.

As shown in FIG. 4, an elastic cap 1 in accordance with the prior art is provided with a bottomed cylindrical shape having an open end portion 2 at one end and a thick bottom wall 3 at the other end and has a receiving hole 4 extending from the open end portion 2 toward the bottom wall 3 therein. The receiving hole 4 receives an annular head 7 of a barrel tip portion 6 provided at the end of a barrel 5 and a puncture needle 8 extending from the end of the barrel tip portion 6.

Specifically, the receiving hole 4 is provided with a large diameter portion 4a, an intermediate diameter portion 4b, and a small diameter portion 4c in that order from the open end portion 2 toward the bottom wall 3. The inner diameter of the large diameter portion 4a is larger than the outer diameter of the annular head 7 formed in the barrel tip portion 6, and the inner diameter of the intermediate diameter portion 4b is substantially equal to the outer diameter of the annular head 7. The small diameter portion 4c is reduced in diameter in a substantially tapered shape from an end of the intermediate diameter portion 4b toward the bottom wall 3 so that the small diameter portion 4c continuously changes from an inner diameter substantially equal to the inner diameter of the intermediate diameter portion 4b to an inner diameter substantially equal to the outer diameter of the puncture needle 8.

When the puncture needle 8 and the barrel tip portion 6 are inserted into the receiving hole 4 as shown in FIG. 5, the puncture needle 8 and the barrel tip portion 6 are moved from the open end portion 2 toward the bottom wall 3 so that the axis of the puncture needle 8 is axially aligned with an axis A of the receiving hole 4 and an insertion direction B of the puncture needle 8 is aligned with the axis A. This allows the tip of the puncture needle 8 to reach a base end surface 3a of the bottom wall 3 through the large diameter portion 4a, the intermediate diameter portion 4b, and the small diameter portion 4c. Thereafter, the puncture needle 8 and the barrel tip portion 6 are further moved as described above, thus inserting the tip of the puncture needle 8 from the base end surface 3a into the bottom wall 3 and sealing the needle hole of the puncture needle 8.

In this regard, the annular head 7 is press-fit into the intermediate diameter portion 4b against the elastic force of the elastic cap 1. Thus, the force (elastic force) by which the increased intermediate diameter portion 4b attempts to return to its original diameter acts on the annular head 7 so that the elastic cap 1 is positioned relative to the tip portion 6 of the barrel 5.

As described above, the elastic cap 1 is detachably mounted to the tip portion 6 of the barrel 5 so as to seal the needle hole of the puncture needle 8 so that a syringe assembly 9 is available. This enables a space between the interior space formed in the barrel 5 and the plunger (not shown) slidably received in the interior space to be filled with a liquid such as a drug in a liquid-tight manner. As described above, the receiving hole 4 has the large diameter portion 4a, the intermediate diameter portion 4b, and the small diameter portion 4c, each having a different inner diameter, where the tip diameter of the small diameter portion 4c having a minimum inner diameter thereof is substantially equal to the outer diameter of the puncture needle 8. As such, there is a concern that inserting the tip of the puncture needle 8 from the base end surface 3a into the bottom wall 3 may become difficult if the axis of the puncture needle 8 is slightly misaligned away from the axis A of the receiving hole 4 or if the insertion direction B is slightly inclined relative to the axis A, upon insertion of the puncture needle 8 and the barrel tip portion 6 into an insertion hole 4.

That is, if the insertion position of the puncture needle 8 is misaligned or the insertion direction B is inclined, it is contemplated that the tip of the puncture needle 8 may be inserted into the side wall of the receiving hole 4 before the tip of the puncture needle 8 reaches the base end surface 3a of the bottom wall 3. In particular, since the small diameter portion 4c is tapered, the puncture needle 8 is likely to be inserted into the side wall of the receiving hole 4. The thickness of the receiving hole 4 is thinner than that of the bottom wall 3. Thus, there is a concern that ensuring an insertion length capable of fully sealing a needle hole may become difficult if the puncture needle 8 is inserted into the side wall of the receiving hole 4.

Furthermore, the end surface of the puncture needle 8 is generally provided with an edge inclined relative to the axis of the puncture needle 8. When such a tip of the puncture needle 8 moves into an elastic member constituting the elastic cap 1, the moving direction thereof is likely to be oriented along the slope of the edge. If the puncture needle 8 is inserted into the side wall of the receiving hole 4, the puncture needle 8 moves in a direction away from the central axis of the elastic cap 1. In this regard, since the elastic cap 1 is less rigid than the puncture needle 8, a tip of the elastic cap 1 is bent opposite to the moving direction of the puncture needle 8 from the central axis of the elastic cap 1, as shown in FIG. 6. When the syringe assembly 9, to which the elastic cap 1 is attached in such a bent condition, is transferred to and from a container accommodating the syringe assembly 9, the tip of the elastic cap 1 may catch the container and this may result in poor yield and a damage of the puncture needle 8.

If the puncture needle 8 is inserted into the thin side wall of the receiving hole 4 as described above, the tip of the puncture needle 8 may eventually penetrate the side wall and be exposed to the outside of the elastic cap 1, as shown in FIG. 7. Moreover, as shown in FIG. 8, if a cover 1a having a high rigidity compared to the puncture needle 8 etc. is attached to the outside of the elastic cap 1, the puncture needle 8 inserted into the side wall of the receiving hole 4 may be bent as it moves.

Furthermore, as described above, the elastic cap 1 is positioned in the syringe assembly 9 by press-fitting the annular head 7 into the intermediate diameter portion 4b having an inner diameter substantially equal to the annular head 7. Thus, it is difficult to accurately define a final insertion position of the barrel tip portion 6 relative to the receiving hole 4. Accordingly, there are concerns that an insertion length of the puncture needle 8 into the bottom wall 3 is insufficient and full sealing of the needle hole may become difficult, for example, if an insertion length of the puncture needle 8 and the barrel tip portion 6 into the receiving hole 4 is short. On the other hand, there are concerns that the puncture needle 8 is inserted into the bottom wall 3 more than necessary and silicone or the like applied to the surface of the puncture needle 6 to improve its lubricity may be removed if the insertion length is long.

That is, there are concerns in the above-described elastic cap 1 that it may become difficult to sufficiently protect the puncture needle 8 and the barrel tip portion 6 and to fully seal the needle hole without damaging the surface of the puncture needle 8 by accurately receiving the puncture needle 8 and the barrel tip portion 6 in the receiving hole 4. There is also a concern that it may become difficult to handle the syringe assembly 9 with the elastic cap 1 attached to the barrel tip portion 6.

SUMMARY OF INVENTION

One objective of certain embodiments of the present invention, which has been made in view of the above problems, is to provide an elastic cap that can sufficiently protect a puncture needle and a barrel tip portion by accurately receiving them in the receiving hole of the elastic cap and can fully seal the needle hole of the puncture needle by receiving the puncture needle having a given length into the bottom wall of the receiving hole.

According to one embodiment, an elastic cap is detachably mounted to a barrel tip portion of a barrel that includes a cylindrical barrel body having an opening at a base end; a barrel tip portion having an annular head and being provided at an end of the barrel body; and a puncture needle having a needle hole and being held in the barrel tip portion so that a tip of the puncture needle projects from the barrel tip portion, the elastic cap sealing a tip of the needle hole. The elastic cap includes a cylindrical receiving hole for receiving at least part of the barrel tip portion and the puncture needle. The receiving hole includes a first inner diameter portion having a smaller diameter than an outer diameter of the annular head; a stopper portion provided at an end of the first inner diameter portion; a second inner diameter portion that is formed from the stopper portion to a bottom portion and has a smaller diameter than the first inner diameter portion; and a bottom wall provided at an end of the second inner diameter portion. The minimum diameter of the receiving hole is 2 to 10 times the outer diameter of the puncture needle. Upon attachment to the barrel tip portion, at least part of the barrel tip portion is inserted into the receiving hole, the first inner diameter portion is in close contact with an outer peripheral surface of the annular head to thereby form an airtight seal between itself and the barrel tip portion, the stopper portion abuts against an end face of the annular head to thereby define a final insertion position of the barrel tip portion, and the tip of the puncture needle is inserted into the bottom wall to thereby seal the tip of the needle hole.

In the embodiment, the minimum diameter of the receiving hole is large compared to the outer diameter of the puncture needle. Thus, the puncture needle could be prevented from being inserted into the side wall of the elastic cap forming the receiving hole if an insertion position is misaligned or an insertion direction is inclined upon insertion of the puncture needle into the receiving hole. Furthermore, the stopper portion is provided between the first inner diameter portion and the second inner diameter portion so that the final insertion position of the barrel tip portion relative to the receiving hole can be easily defined. That is, since the end face of the annular head abuts against the stopper portion when the barrel tip portion reaches the final insertion position, the barrel tip portion can be easily prevented from entering the receiving hole beyond the final insertion position.

Therefore the elastic cap can accurately receive the puncture needle and the barrel tip portion in the receiving hole with the puncture needle having a given length inserted into the bottom wall of the receiving hole. Thus, the elastic cap can fully seal the needle hole without damaging the surface of the puncture needle as well as provide good protection for the puncture needle and the barrel tip portion.

In one aspect, the elastic cap is characterized in that an inner peripheral surface of the second inner diameter portion is not contacted with the tip of the puncture needle upon attachment to the barrel tip portion. As described above, the minimum diameter of the receiving hole is large enough compared to the outer diameter of the puncture needle so that the tip of the puncture needle can be effectively prevented from making contact with the inner peripheral surface of the second inner diameter portion when the tip of the puncture needle is inserted into the receiving hole. That is, the tip of the puncture needle can be prevented from being inserted into the side wall of the elastic cap. This can effectively prevent, for example, the elastic cap from being deformed, the tip of the puncture needle from projecting from the side wall of the elastic cap, and the puncture needle from bending in the side wall of the elastic cap due to the attachment of the elastic cap to the barrel tip portion.

In one aspect, the elastic cap is characterized in that a base end surface of the bottom wall is a concave sphere toward an end, a center of the sphere is on an axis of the receiving hole, and a radius of the sphere is substantially equal to a length from a proximal end to a distal end of a portion projecting from the barrel tip portion of the puncture needle. In this case, in which the base end surface of the bottom wall is curved as described above, an insertion length of the puncture needle into the bottom wall can be kept constant even if the puncture needle is inserted at any point of the base end surface upon insertion of the barrel tip portion of the barrel to the final insertion position in the receiving hole. In other words, a constant insertion length into the bottom wall can be ensured even if an insertion direction or an insertion position is misaligned upon insertion of the puncture needle into the receiving hole. This enables the needle hole of the puncture needle to be fully sealed and the puncture needle to be held firmly in the elastic cap.

In one aspect, the elastic cap is characterized in that a length from the base end surface of the bottom wall to the stopper portion is 2 to 7 mm shorter than the length from the proximal end to the distal end of the portion projecting from the barrel tip portion of the puncture needle. In this case, a length by which the puncture needle is inserted into the bottom wall of the receiving hole may be 2 to 7 mm. In this manner, ensuring a length of the puncture needle inserted into the bottom wall, i.e., an insertion length, more than or equal to 2 mm enables the needle hole of the puncture needle to be fully sealed. Moreover, ensuring an insertion length of the puncture needle less than or equal to 7 mm enables friction between the surface of the puncture needle and the bottom wall to be reduced when the puncture needle is inserted into the bottom wall. Thus, removal of silicone due to the friction could be prevented if, for example, silicone or the like is applied to the surface of the puncture needle to improve its lubricity. Consequently, an increase in piercing resistance of the puncture needle can be avoided.

In one aspect, the elastic cap is characterized in that the inner peripheral surface of the second inner diameter portion extends about the axis of the receiving hole. In this case, the barrel tip portion and the puncture needle can be inserted into the receiving hole along the extending direction of the inner peripheral surface. This can effectively prevent the puncture needle from being inserted into the side wall of the elastic cap, for example, as compared to the use of a tapered inner peripheral surface. Thus, upon insertion of the barrel tip portion and the puncture needle into the receiving hole, the barrel tip portion and the puncture needle can be accurately received in the receiving hole with the puncture needle properly inserted into the bottom wall. That is, the needle hole of the puncture needle can be fully sealed and the puncture needle and the barrel tip portion can be well protected in the receiving hole.

In one aspect, the elastic cap is characterized in that the receiving hole has a third inner diameter portion having a diameter larger than the outer diameter of the annular head in its base end, a length from the base end surface of the bottom wall to an end of the third inner diameter portion is longer than a length from the tip of the puncture needle to an end of the annular head, and a difference between an inner diameter of the third inner diameter portion and the outer diameter of the annular head is smaller than a difference between an inner diameter of the second inner diameter portion and the outer diameter of the puncture needle. In this case, the puncture needle and the barrel tip portion are inserted into the third inner diameter portion having the diameter larger than the puncture needle and the barrel tip portion before the puncture needle and the barrel tip portion are inserted into the first and second inner diameter portions so that misalignment of the insertion position and inclination of the insertion direction can be reduced. This can effectively prevent the puncture needle from being inserted into the side wall of the elastic cap and enables the puncture needle to be accurately and easily inserted into the bottom wall. Thus, the needle hole of the puncture needle can be fully sealed and the puncture needle and the barrel tip portion can be well protected in the receiving hole.

In one aspect, the elastic cap is characterized in that the receiving hole has a temporary stopper portion between the third inner diameter portion and the first inner diameter portion, a length from the base end surface of the bottom wall to the temporary stopper portion is longer than the length from the proximal end to the distal end of the puncture needle portion projecting from the barrel tip portion, and the temporary stopper portion abuts against the end face of the annular head upon attachment to the barrel tip portion so that the insertion of the barrel tip portion into the receiving hole is temporarily stopped and the axis of the receiving hole is substantially aligned with an axis of the puncture needle. In this case, the end face of the annular head first abuts against the temporary stopper portion when the puncture needle and the barrel tip portion are inserted into the receiving hole. This enables the puncture needle and the barrel tip portion to be inserted toward the first inner diameter portion and the second inner diameter portion with the axis of the receiving hole being substantially aligned with the axis of the puncture needle. Consequently, the puncture needle can be more effectively prevented from being inserted into the side wall of the elastic cap and the puncture needle can be accurately and easily inserted into the bottom wall of the receiving hole so that the needle hole of the puncture needle can be fully sealed and the puncture needle and the barrel tip portion can be well protected.

A syringe assembly embodiment is characterized in that it includes the elastic cap according described above and the barrel to which the elastic cap is detachably mounted, the tip of the needle hole being sealed by insertion of the tip of the puncture needle into the bottom wall.

Certain embodiments of the present invention, in which the elastic cap is configured to be attached to the barrel tip portion, effectively prevent, for example, the elastic cap from being deformed, the tip of the puncture needle from projecting from the side wall of the elastic cap, and the puncture needle from bending in the side wall of the elastic cap. That is, the accurate attachment of the elastic cap to the barrel tip portion in the syringe assembly allows easy handling.

In one aspect, the syringe assembly is characterized in that a length by which the puncture needle is inserted into the bottom wall is from 2 to 7 mm. In this case, the elastic cap can provide good protection for the puncture needle and fully seal the puncture needle. This allows the barrel to be filled with a liquid such as a drug in a liquid-tight manner.

DETAILED DESCRIPTION

A syringe assembly according to an embodiment of the present invention will now be described in detail with reference the accompanying drawings.

Figure 1:
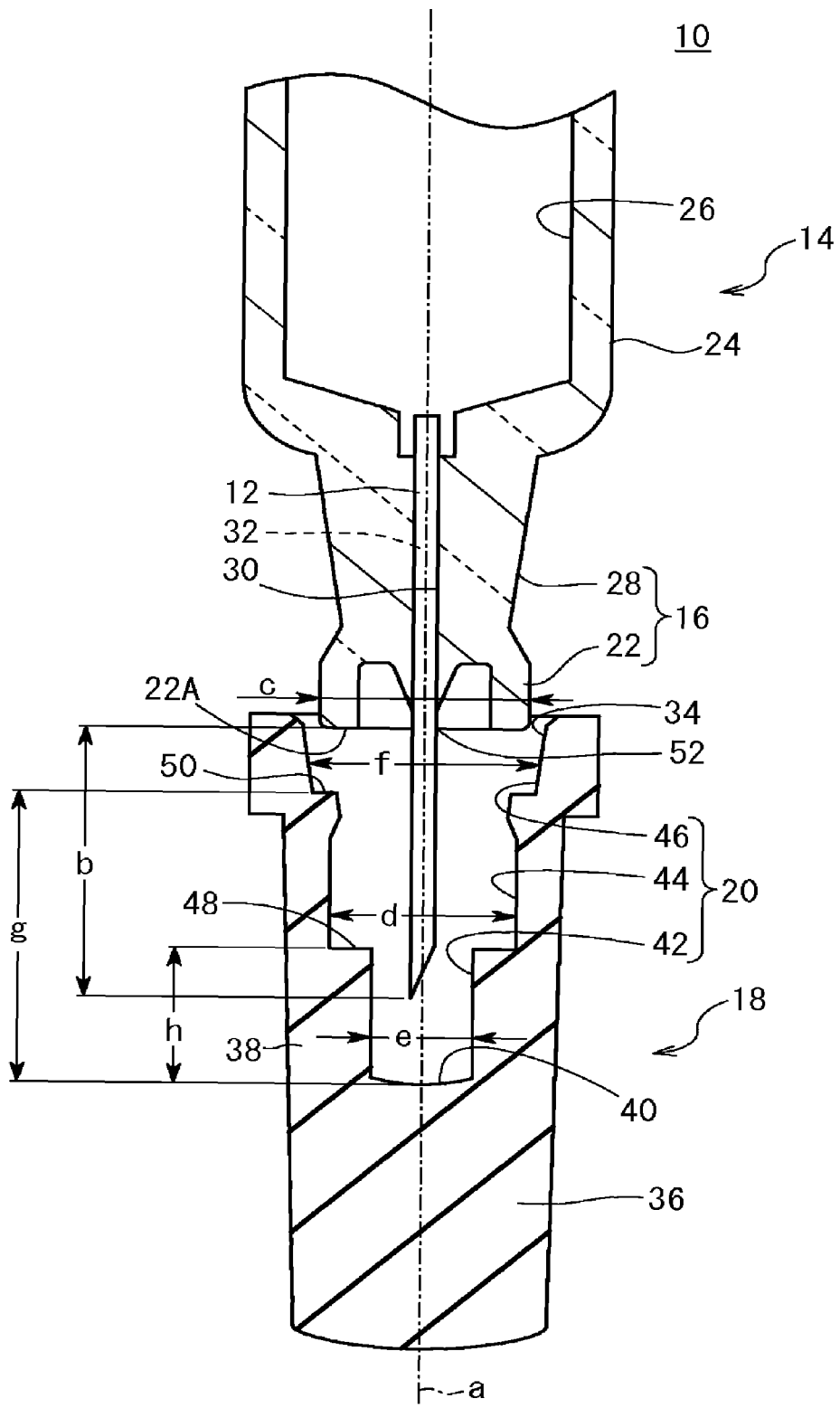
FIG. 1 is a schematic longitudinal sectional view illustrating a syringe assembly according to a present embodiment before an elastic cap is attached to the tip portion of a barrel.

FIG. 1 is a schematic longitudinal sectional view illustrating a syringe assembly 10 according to a present embodiment before an elastic cap 18 is attached to a tip portion 16 of a barrel 14 having a puncture needle 12. Referring first to FIG. 1, the configuration of the syringe assembly 10 is described.

In the syringe assembly 10, the elastic cap 18 is detachably mounted to the tip portion 16 of the barrel 14, for example, before a plunger (not shown) is mounted in an interior space 26 of the barrel 14 constituting a syringe. That is, the syringe assembly 10, which includes the barrel 14, the puncture needle 12, and the elastic cap 18, is configured to receive the puncture needle 12 and a part of the tip portion 16 of the barrel 14 in a receiving hole 20 formed in the elastic cap 18.

The barrel 14 is transparent or translucent and is a cylindrical body, which is preferably made of a material having low oxygen permeability and low water vapor permeability, for example, resins, such as polypropylene, polyethylene, polystyrene, polyamide, polycarbonate, polyvinyl chloride, poly-(4-methylpentene-1), acrylic resin, acrylonitrile-butadiene-styrene copolymer, polyester such as polyethylene terephthalate, cyclic polyolefin etc., glass, and the like.

The barrel 14 includes a barrel body 24 having an opening (not shown) at a base end, the barrel tip portion 16 having an annular head 22 and being provided at the end of the barrel body 24, and the puncture needle 12 held in the barrel tip portion 16 so that the tip of the puncture needle 12 projects from the annular head 22.

The barrel body 24 has a diameter larger than the barrel tip portion 16 and is provided with the interior space 26 therein. The barrel tip portion 16 is provided with the annular head 22 having a substantially uniform diameter along the longitudinal direction of the barrel tip portion 16 and a tapered portion 28 that is tapered first to a smaller diameter from the base end side of the annular head 22 and then to a larger diameter toward the barrel body 24. A press-fit hole 30 connected to the interior space 26 is formed from the annular head 22 to the barrel body 24, and the puncture needle 12 is held in position in the barrel tip portion 16 by being press-fit into the press-fit hole 30.

After attachment of the elastic cap 18 to the barrel tip portion 16 (see FIG. 3), a space between the plunger (not shown) slidably mounted in the interior space 26 and the interior space 26 is filled with a liquid or the like, and thus a prefilled syringe is provided.

The puncture needle 12, which is, for example, about 0.4 mm in outer diameter, is provided with a needle hole 32 that is formed through the puncture needle 12 in its longitudinal direction. The needle hole 32 is in communication with the interior space 26 of the barrel 14.

The elastic cap 18 is formed of an elastic member made of, for example, rubber, such as isoprene rubber, butyl rubber, latex rubber, silicone rubber, etc. or synthetic resin, such as SBS elastomer, SEBS elastomer, polyolefin elastomer, etc. The elastic cap 18 has a bottomed cylindrical shape including an open end portion 34 at one end and a thick bottom wall 36 at the other end. That is, the receiving hole 20 extending about the axis of the elastic cap 18 is formed on the inside of the bottom wall 36 of the elastic cap 18 and a side wall 38 extending from the bottom wall 36 toward the open end portion 34. The puncture needle 12 and the tip portion 16 of the barrel 14 can be inserted into the receiving hole 20 from the open end portion 34 toward the bottom wall 36.

The bottom of the receiving hole 20, i.e., a base end surface 40 of the bottom wall 36 is shaped as a concave sphere toward the end of the elastic cap 18. The center of the sphere is on an axis a of the receiving hole 20, and the radius of the sphere is substantially equal to a length b from a proximal end 52 to a distal end of the puncture needle 12 projecting from the barrel tip portion 16.

The receiving hole 20 includes a small diameter portion (second inner diameter portion) 42, an intermediate diameter portion (first inner diameter portion) 44, and a large diameter portion (third inner diameter portion) 46 in that order from the base end surface 40 toward the open end portion 34, each portion having a different inner diameter. Specifically, the receiving hole 20 includes the intermediate diameter portion 44 having an inner diameter d smaller than an outer diameter c of the annular head 22; a stopper portion 48 provided at the end of the intermediate diameter portion 44; the small diameter portion 42 that is formed from the stopper portion 48 toward the bottom wall 36 and has an inner diameter e smaller than the inner diameter d of the intermediate diameter portion 44; and the large diameter portion 46 having an inner diameter f larger than the outer diameter c of the annular head 22.

The small diameter portion 42 is a portion where an inner diameter of the receiving hole 20 is minimum, and the inner diameter e of the small diameter portion 42 is 2 to 10 times the outer diameter of the puncture needle 12. Therefore, when the outer diameter of the puncture needle 12 is, for example, about 0.4 mm, the inner diameter e of the small diameter portion 42 is about 0.8 to 4 mm. The inner diameter e of the small diameter portion 42 is substantially uniform from the base end surface 40 toward the open end portion 34. That is, the inner peripheral surface of the side wall 38 forming the small diameter portion 42 extends parallel to the axis a of the receiving hole 20. A difference between the inner diameter f of the large diameter portion 46 and the outer diameter c of the annular head 22 is small compared to a difference between the inner diameter e of the small diameter portion 42 and the outer diameter of the puncture needle 12.

The stopper portion 48 is formed on the inside of the side wall 38 and between the small diameter portion 42 and the intermediate diameter portion 44, the stopper portion 48 being stepped due to a difference between the inner diameters thereof. The present embodiment is configured so that a length h from the base end surface 40 of the bottom wall 36 to the stopper portion 48 is 2 to 7 mm shorter than the length b from the proximal end 52 to the distal end of the puncture needle 12 projecting from the barrel tip portion 16. A temporary stopper portion 50 is likewise formed between the intermediate diameter portion 44 and the large diameter portion 46, and a length g from the base end surface 40 of the bottom wall 36 to the temporary stopper portion 50 (i.e., a length from the base end surface 40 to the end of the large diameter portion 46) is longer than the length b of the puncture needle 12.

As described below, the end face 22A of the annular head 22 is configured to abut against the stopper portion 48 and the temporary stopper portion 50 upon insertion of the barrel tip portion 16 into the receiving hole 20. In other words, when the barrel tip portion 16 is inserted into the receiving hole 20 to a final insertion position and the elastic cap 18 is detachably mounted to the barrel tip portion 16, the temporary stopper portion 50 temporarily stops the entry of the barrel tip portion 16 into the receiving hole 20 and the stopper portion 48 restricts the entry of the barrel tip portion 16 into the receiving hole 20 beyond the final insertion position.

The process of removably attaching the elastic cap 18 to the tip portion 16 of the barrel 14 in the syringe assembly 10 is described below.

First, as shown in FIG. 1, the elastic cap 18 and the barrel 14 are relatively positioned so that the axis of the puncture needle 12 is aligned with the axis a of the receiving hole 20 and the tip of the puncture needle 12 faces the open end portion 34. The elastic cap 18 and the barrel 14 are then relatively moved toward each other along the axis a so that the puncture needle 12 and the tip portion 16 of the barrel 14 are inserted into the receiving hole 20.

Figure 2:
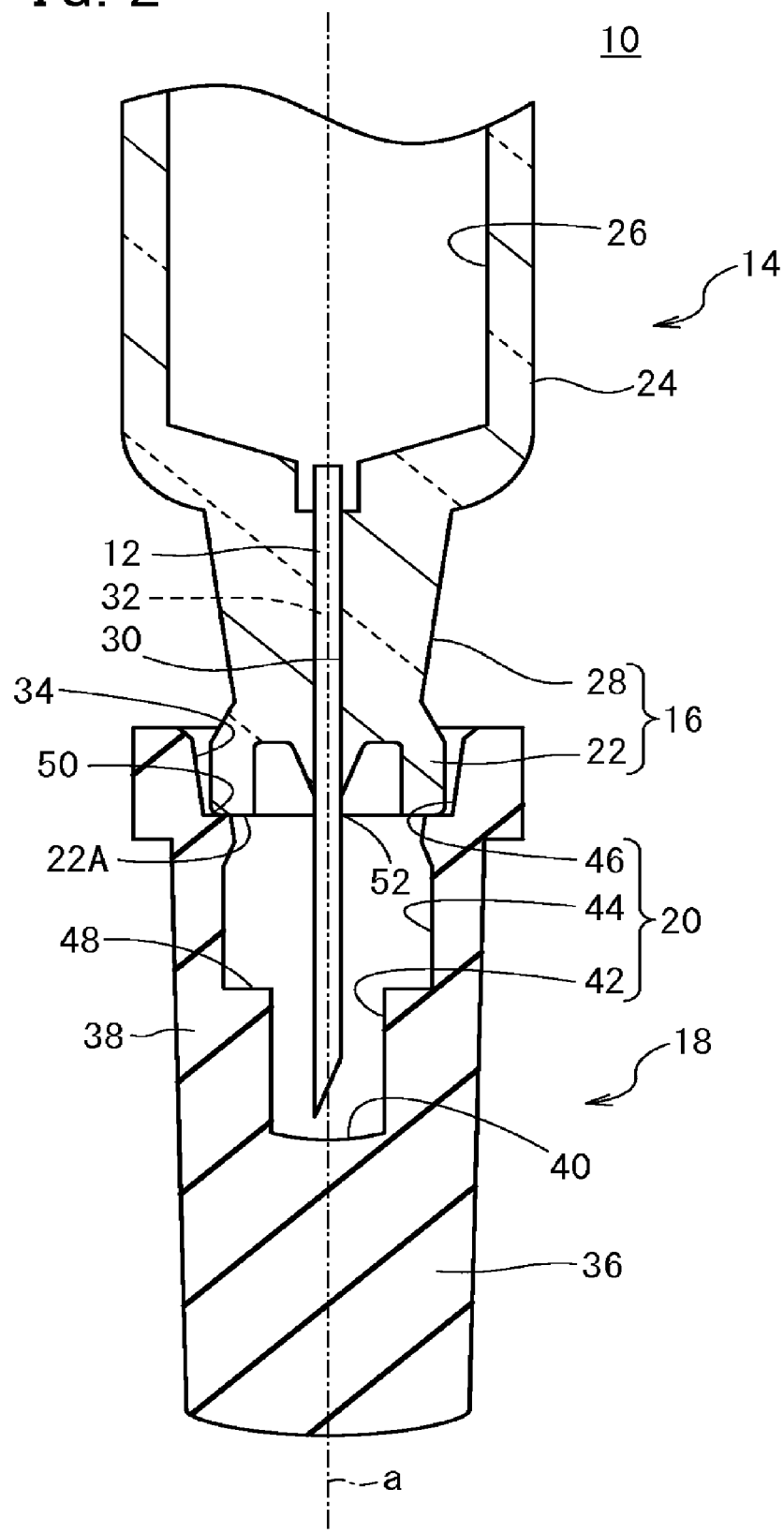
FIG. 2 is a schematic longitudinal sectional view illustrating the syringe assembly shown in FIG. 1, where the tip portion of the barrel and a puncture needle are inserted into a receiving hole of the elastic cap.

In this regard, before the puncture needle 12 and the barrel tip portion 16 are inserted into the intermediate diameter portion 44 and the small diameter portion 42, they are first inserted into the large diameter portion 46 having a larger diameter than the intermediate diameter portion 44 and the small diameter portion 42. The inner diameter f of the large diameter portion 46 is larger than the outer diameter c of the annular head 22, and the difference between the inner diameter f of the large diameter portion 46 and the outer diameter c of the annular head 22 is small compared to the difference between the inner diameter e of the small diameter portion 42 and the outer diameter of the puncture needle 12. This reduces misalignment of the puncture needle 12 and the barrel tip portion 16 and inclination of the insertion direction relative to the receiving hole 20. Thereafter, as shown in FIG. 2, the end face 22A of the annular head 22 inserted into the large diameter portion 46 of the receiving hole 20 abuts against the temporary stopper portion 50 so that the insertion of the puncture needle 12 and the barrel tip portion 16 is temporarily stopped. That is, since the insertion is once stopped, the puncture needle 12 and the barrel tip portion 16 can be sequentially positioned relative to the receiving hole 20. Thus, the puncture needle 12 and the barrel tip portion 16 is further inserted toward the intermediate diameter portion 44 and the small diameter portion 42 with the axis a of the receiving hole 20 being substantially aligned with the axis of the puncture needle 12.

When the end face 22A of the annular head 22 reaches the temporary stopper portion 50, the tip of the puncture needle 12 is inserted into the small diameter portion 42 through the large diameter portion 46 and the intermediate diameter portion 44. As described above, the inner diameter e of the small diameter portion 42, which is a minimum diameter portion of the receiving hole 20, is 2 to 10 times the outer diameter of the puncture needle 12, i.e., the inner diameter e is large enough compared to the outer diameter of the puncture needle 12, and the inner peripheral surface of the side wall 38 forming the small diameter portion 42 extends about the axis a. Therefore the inner peripheral surface of the small diameter portion 42 does not make contact with the tip of the puncture needle 12 when the tip of the puncture needle 12 is inserted into the small diameter portion 42. Thus, the tip of the puncture needle 12 is prevented from being inserted into the side wall 38 of the receiving hole 20.

When the barrel tip portion 16 is then further advanced into the receiving hole 20, elastic deformation of the temporary stopper portion 50 allows the annular head 22 to enter the intermediate diameter portion 44. That is, the annular head 22 is press-fit into the intermediate diameter portion 44 having an inner diameter d slightly smaller than the outer diameter c of the annular head 22 against the elastic force of the elastic cap 18. In this regard, the inner peripheral surface of the intermediate diameter portion 44 is in close contact with the outer peripheral surface of the annular head 22 so that an airtight seal is formed between the intermediate diameter portion 44 and the barrel tip portion 16, and the tip of the puncture needle 12 is inserted into the bottom wall 36 from the base end surface 40.

Figure 3:
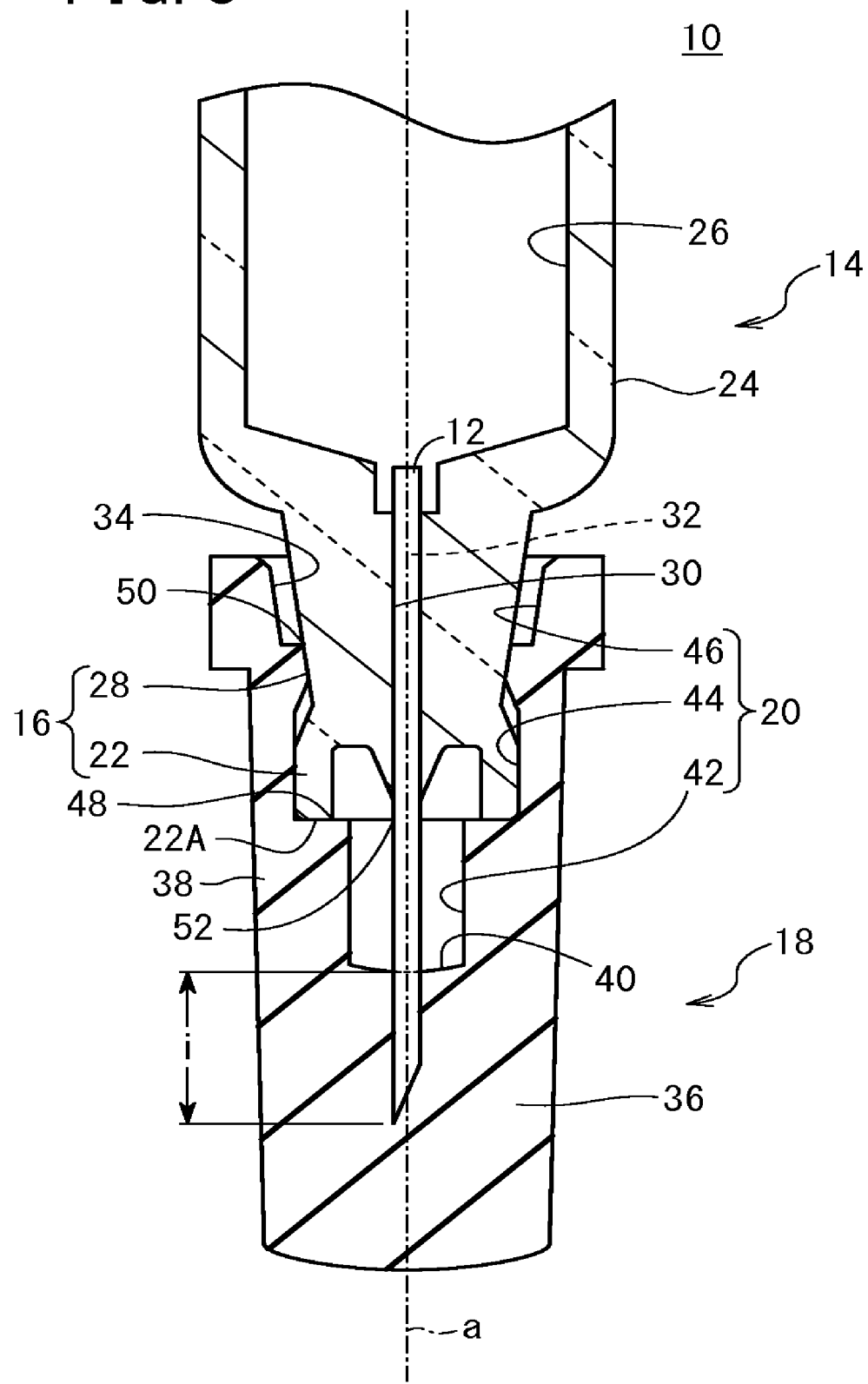
FIG. 3 is a schematic longitudinal sectional view illustrating the syringe assembly shown in FIG. 1, where the elastic cap is detachably mounted to the tip portion of the barrel.
Figure 4:
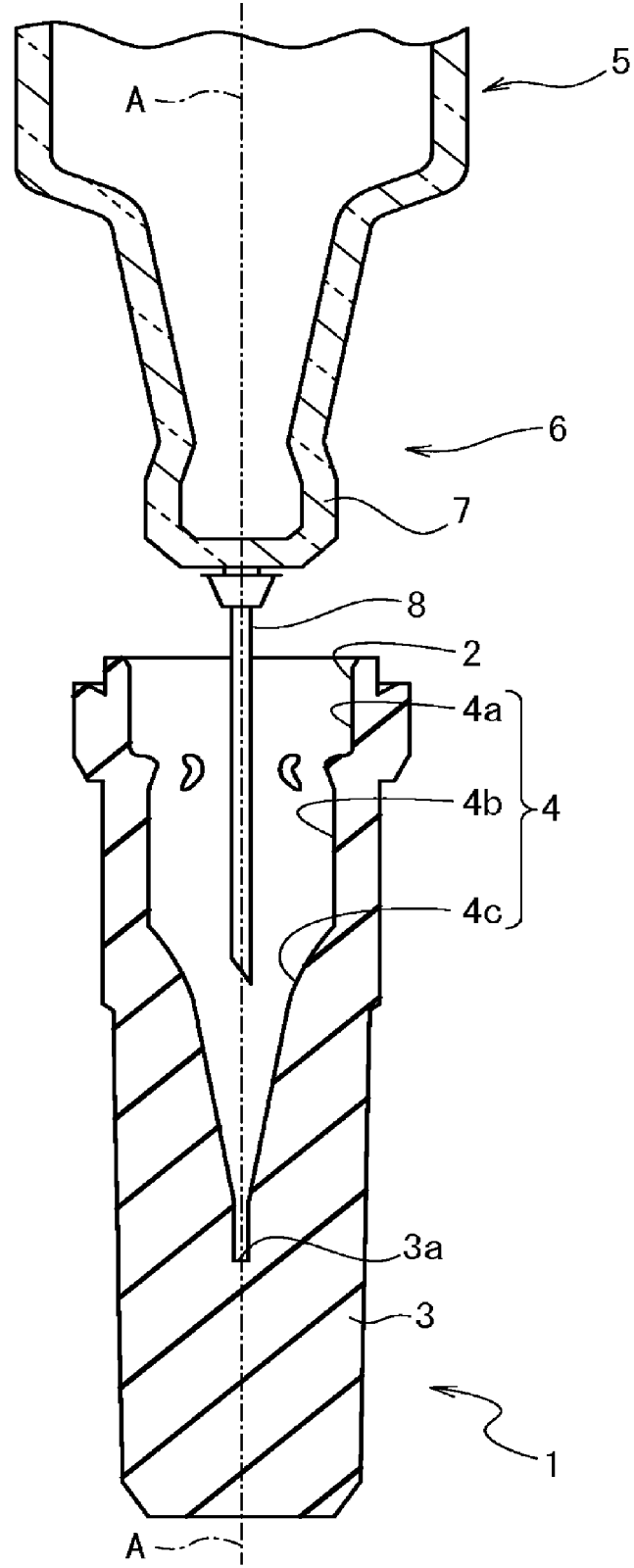
FIG. 4 is a schematic longitudinal sectional view showing a process for obtaining a syringe assembly, where a conventional elastic cap is not yet attached to the tip portion of a barrel having a puncture needle.
Figure 5:
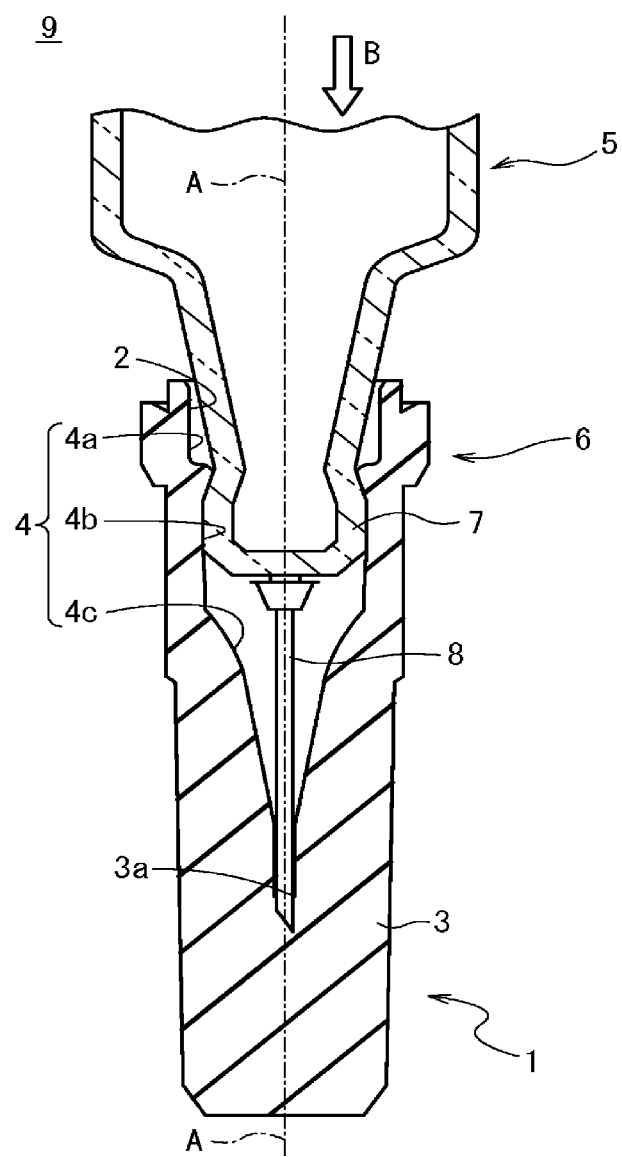
FIG. 5 is schematic longitudinal sectional view showing a process for obtaining the syringe assembly, where the conventional elastic cap is attached to the tip portion of the barrel having the puncture needle.
Figure 6:
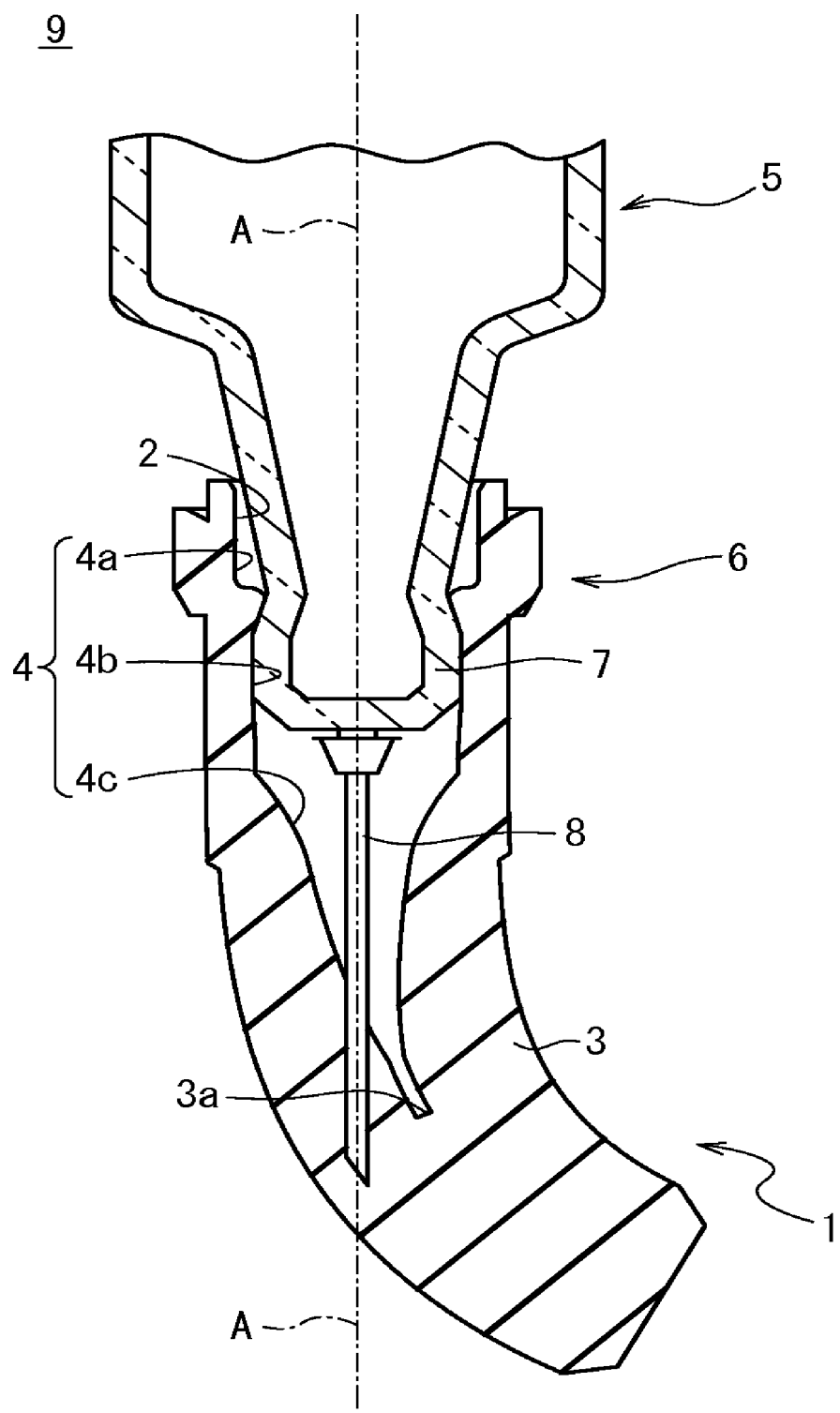
FIG. 6 is a schematic longitudinal sectional view illustrating deformation of the conventional elastic cap.
Figure 7:
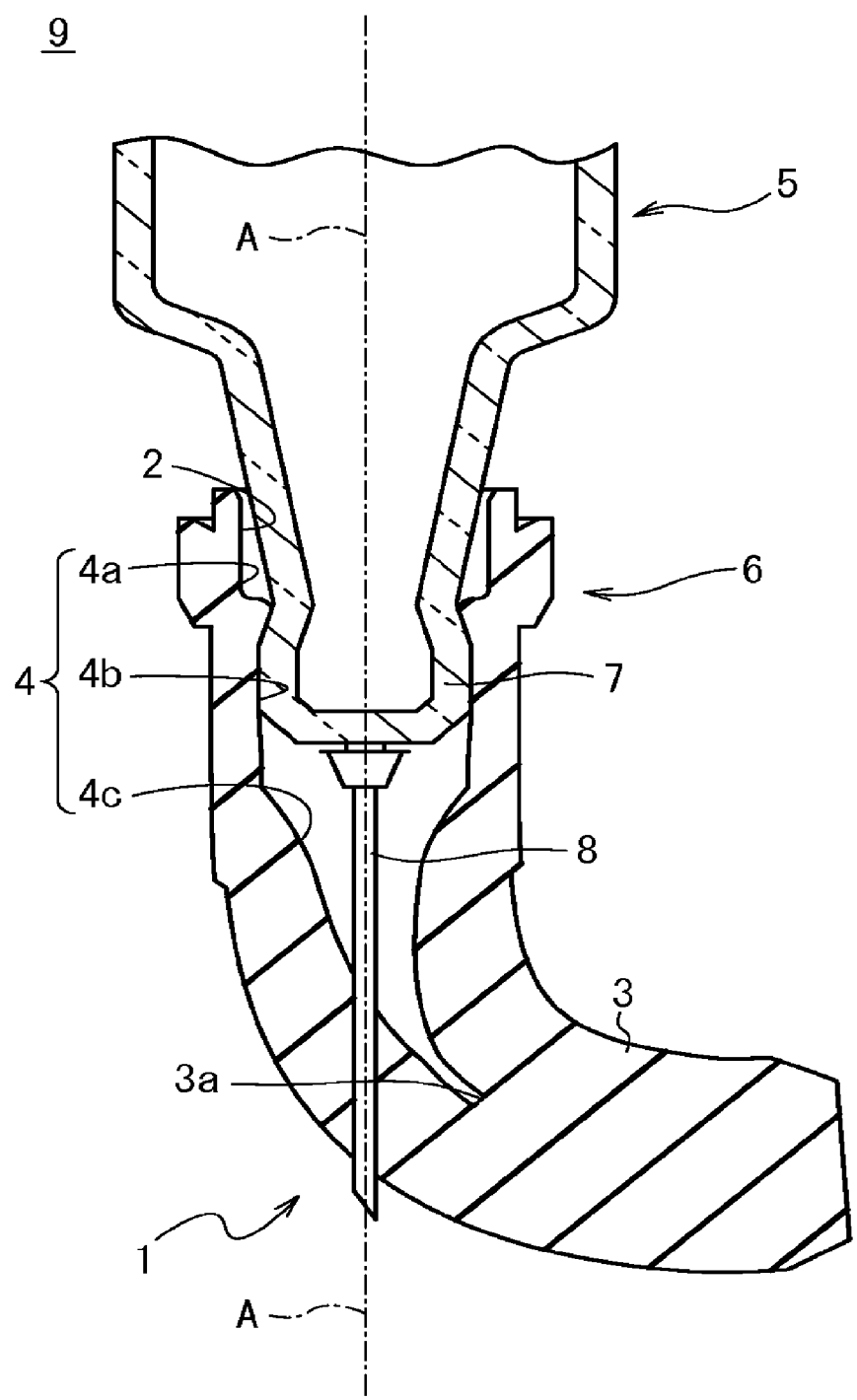
FIG. 7 is a schematic longitudinal sectional view illustrating the puncture needle exposed to the outside of the conventional elastic cap deformed.
Figure 8:
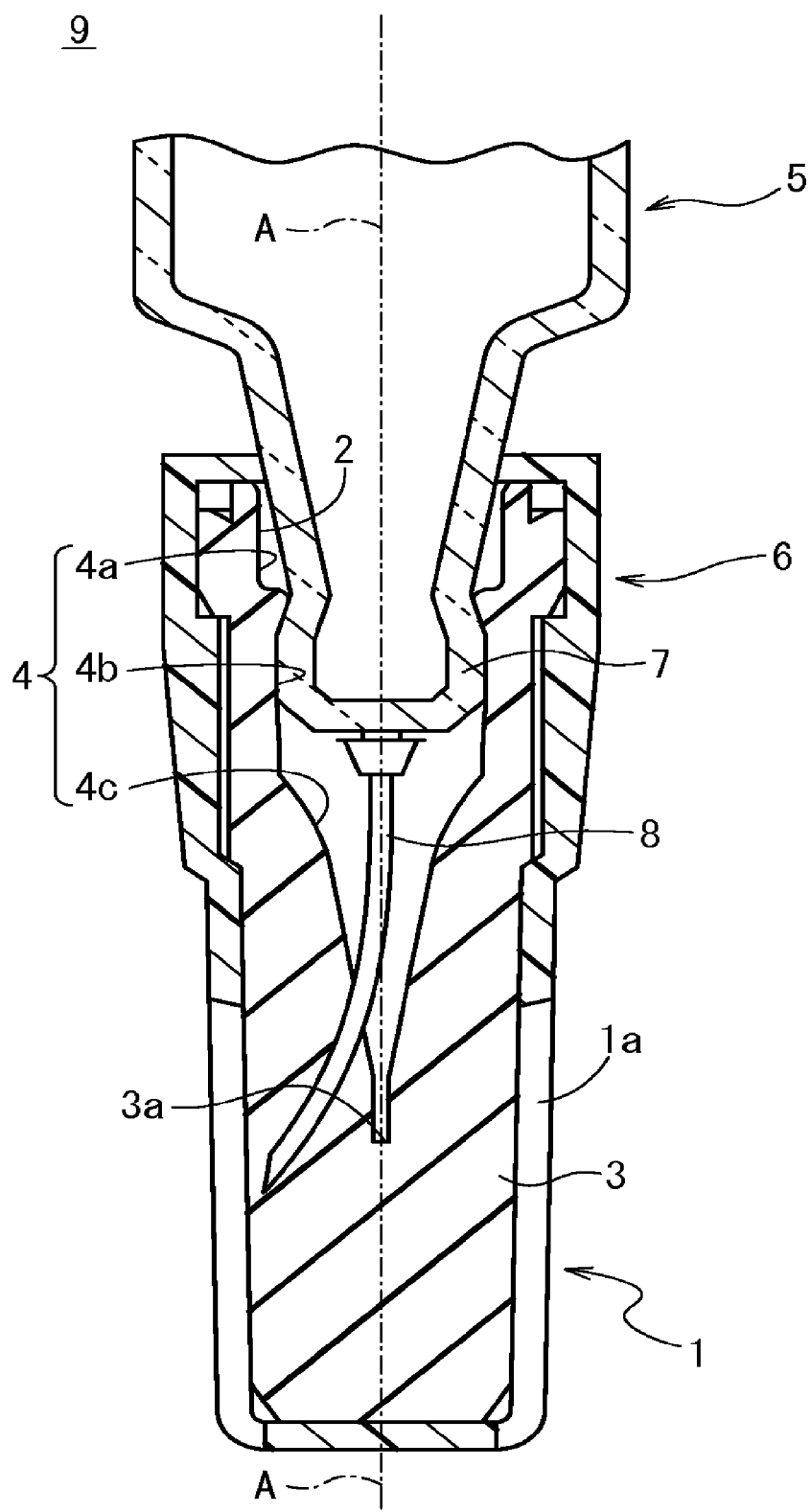
FIG. 8 is a schematic longitudinal sectional view illustrating a puncture needle that is deformed in the side wall of a conventional elastic cap with a cover.

When the annular head 22 enters the intermediate diameter portion 44 and finally reaches the final insertion position as shown in FIG. 3, the end face 22A of the annular head 22 abuts against the stopper portion 48. This restricts further movement of the barrel tip portion 16 into the receiving hole 20.

As described above, the base end surface 40 is shaped as a sphere of which the radius is substantially equal to the length b from the proximal end 52 to the distal end of the puncture needle 12 projecting from the barrel tip portion 16. As such, an insertion length i of the puncture needle 12 into the bottom wall 36 can be kept constant even if the puncture needle 12 is inserted at any point of the base end surface 40 upon insertion of the barrel tip portion 16 to the final insertion position in the receiving hole 20. In other words, when the puncture needle 12 is inserted into the small diameter portion 42, the insertion length i into the bottom wall 36 could be kept constant if the extending direction of the puncture needle 12 is not exactly aligned with the axis a or it is inclined relative to the axis a. This enables the needle hole 32 of the puncture needle 12 to be fully sealed and a given insertion length i through which the puncture needle 12 is held firmly in the elastic cap 18 to be ensured.

As described above, the present embodiment is configured so that the length h from the base end surface 40 of the bottom wall 36 to the stopper portion 48 is 2 to 7 mm shorter than the length b from the proximal end 52 to the distal end of the puncture needle 12 projecting from the barrel tip portion 16. The insertion length i may be 2 to 7 mm accordingly.

In this manner, ensuring the insertion length i of the puncture needle 12 more than or equal to 2 mm enables the needle hole 32 of the puncture needle 12 to be fully sealed. Moreover, ensuring the insertion length i of the puncture needle 12 less than or equal to 7 mm enables friction between the surface of the puncture needle 12 and the elastic cap 18 to be reduced when the puncture needle 12 is inserted into the bottom wall 36. Thus, removal of silicone due to the friction could be prevented if, for example, silicone or the like is applied to the surface of the puncture needle 12 to improve its lubricity. Consequently, an increase in piercing resistance of the puncture needle 12 can be avoided.

When the barrel tip portion 16 is inserted to the final insertion position, most of the tapered portion 28 is inserted into the large diameter portion 46 and the intermediate diameter portion 44. As noted above, the annular head 22 is press-fit into the intermediate diameter portion 44 having an inner diameter d slightly smaller than the outer diameter c of the annular head 22 against the elastic force of the elastic cap 18. Consequently, the elastic force, by which the increased intermediate diameter portion 44 attempts to return to its original diameter, acts on the annular head 22. Furthermore, combined with the close contact of the temporary stopper portion 50 with the outer peripheral surface of the tapered portion 28, the elastic cap 18 is positioned on the tip portion 16 of the barrel 14. Thus, the elastic cap 18 is detachably mounted to the tip portion 16 of the barrel 14.

As described above, the syringe assembly 10 according to the present embodiment can accurately receive the puncture needle 12 and the barrel tip portion 16 in the receiving hole 20 with the given insertion length i of the puncture needle 12 being inserted into the bottom wall 36 of the receiving hole 20. This enables the needle hole 32 of the puncture needle 12 to be fully sealed and the puncture needle 12 and the barrel tip portion 16 to be sufficiently protected.

While the present invention has been described above with reference to an embodiment, the present invention is not limited thereto. It should be understood that various modifications can be made without departing from the scope of the invention.

For example, while a prefilled syringe is provided in the embodiment, the syringe assembly 10 is not limited to one for the prefilled syringe and other syringes could be provided.

What is claimed is:

1. A syringe assembly comprising:
a barrel assembly comprising:
a cylindrical barrel body having an opening at a base end;
a barrel tip portion having an annular head and being disposed at an end of the barrel body; and
a puncture needle having a needle hole and being held in the barrel tip portion such that a tip of the puncture needle projects from the barrel tip portion; and
an elastic cap that is detachably mountable to the barrel tip portion of the barrel assembly, the elastic cap comprising:
a closed bottom wall at a distal end of the elastic cap,
an open end portion at a proximal end of the elastic cap,
a side wall extending from the bottom wall toward the open end portion, and
a cylindrical receiving hole formed by the bottom wall, the side wall, and the open end portion, the receiving hole being configured to receive at least part of the barrel tip portion and the puncture needle,
wherein the bottom wall has a base end surface that faces the receiving hole, and
wherein the receiving hole includes:
a first inner diameter portion having an inner diameter that is smaller than an outer diameter of the annular head;
a stopper portion disposed at a distal end of the first inner diameter portion; and
a second inner diameter portion that extends from the stopper portion to said base end surface, an inner diameter of the second inner diameter portion being smaller than the inner diameter of the first inner diameter portion,
wherein a minimum of the inner diameter of the second inner dinner portion is twice or greater than an outer diameter of the puncture needle,
wherein the elastic cap is configured such that, upon attachment to the barrel tip portion, at least part of the barrel tip portion is inserted into the receiving hole, the first inner diameter portion is in close contact with an outer peripheral surface of the annular head such that an airtight seal is formed between the first inner diameter portion and the barrel tip portion, the stopper portion abuts a distal end face of the annular head such that the stopper portion defines a final insertion position of the barrel tip portion, and the tip of the puncture needle penetrates the bottom wall through the base end surface of the bottom wall such that the bottom wall seals the tip of the puncture needle.

2. The syringe assembly according to claim 1, wherein the elastic cap is configured such that an inner peripheral surface of the second inner diameter portion does not contact the tip of the puncture needle upon attachment of the elastic cap to the barrel tip portion.

3. The syringe assembly according to claim 1,
wherein the base end surface of the bottom wall is shaped as a portion of a concave sphere,
wherein a center of the sphere is aligned with an axis of the receiving hole, and
wherein a radius of the sphere is substantially equal to a length of a portion of the puncture needle that projects from the barrel tip portion.

4. The syringe assembly according to claim 1, wherein a length from the base end surface of the bottom wall to the stopper portion is 2 to 7 mm shorter than a length of the puncture needle that projects from the barrel tip portion.

5. The syringe assembly according to claim 1, wherein an inner peripheral surface of the second inner diameter portion extends about an axis of the receiving hole.

6. The syringe assembly according to claim 1,
wherein the receiving hole has, at its proximal end, a third inner diameter portion having an inner diameter that is larger than the outer diameter of the annular head,
wherein a length from the base end surface of the bottom wall to a distal end of the third inner diameter portion is longer than a length from the tip of the puncture needle to a distal end of the annular head, and
wherein a difference between the inner diameter of the third inner diameter portion and the outer diameter of the annular head is smaller than a difference between the inner diameter of the second inner diameter portion and the outer diameter of the puncture needle.

7. The syringe assembly according to claim 6,
wherein the receiving hole has a temporary stopper portion between the third inner diameter portion and the first inner diameter portion,
wherein a length from the base end surface of the bottom wall to the temporary stopper portion is longer than the length from the tip of the puncture needle to the distal end of the annular head, and
wherein the elastic cap is configured such that the temporary stopper portion abuts against the distal end face of the annular head upon attachment to the barrel tip portion such that insertion of the barrel tip portion into the receiving hole is temporarily stopped, and an axis of the receiving hole is substantially aligned with an axis of the puncture needle.

8. The syringe assembly according to claim 7,
wherein the base end surface of the bottom wall is shaped as a portion of a concave sphere,
wherein a center of the sphere is aligned with an axis of the receiving hole, and
wherein a radius of the sphere is substantially equal to the length of a portion of the puncture needle that projects from the barrel tip portion.

9. The syringe assembly according to claim 8, wherein a length from the base end surface of the bottom wall to the stopper portion is 2 to 7 mm shorter than the length of the puncture needle that projects from the barrel tip portion.

10. The syringe assembly according to claim 9, wherein the inner peripheral surface of the second inner diameter portion extends about an axis of the receiving hole.

11. The syringe assembly according to claim 10, wherein the elastic cap is configured such that an inner peripheral surface of the second inner diameter portion does not contact the tip of the puncture needle upon attachment of the elastic cap to the barrel tip portion.

12. The syringe assembly according to claim 1, wherein the inner diameter of the second inner diameter portion is substantially uniform from the stopper portion to the base end surface.

13. The syringe assembly according to claim 1, wherein a length by which the puncture needle penetrates the bottom wall is from 2 to 7 mm.

14. The syringe assembly according to claim 1, further comprising a plunger, and a drug disposed in the barrel body.

15. A syringe assembly comprising:
   a barrel assembly comprising:
      a cylindrical barrel body having an opening at a base end;
      a barrel tip portion having an annular head and being disposed at an end of the barrel body; and
      a puncture needle having a needle hole and being held in the barrel tip portion such that a tip of the puncture needle projects from the barrel tip portion; and
   a cap mounted on the barrel tip portion of the barrel assembly, the cap comprising:
      a closed bottom wall at a distal end of the cap,
      an open end portion at a proximal end of the cap,
      a side wall extending from the bottom wall toward the open end portion, and
      a cylindrical receiving hole formed by the bottom wall, the side wall, and the open end portion, the receiving hole being configured to receive at least part of the barrel tip portion and the puncture needle,
   wherein the bottom wall has a base end surface that faces the receiving hole, and
   wherein the receiving hole includes:
      a first portion having an inner diameter that is smaller than an outer diameter of the annular head;
      a stopper portion disposed at a distal end of the first portion;
      a second portion that extends from the stopper portion to said base end surface, an inner diameter of the second portion being smaller than the inner diameter of the first portion;
      a third portion disposed at a proximal end of the receiving hole; and
      a temporary stopper portion disposed between the third portion and the first portion and configured to deform elastically,
   wherein a minimum of the inner diameter of the second portion is twice or greater than an outer diameter of the puncture needle,
   wherein the cap is configured such that, upon attachment to the barrel tip portion, at least part of the barrel tip portion is inserted into the receiving hole, the first portion is in contact with an outer peripheral surface of the annular head, the stopper portion abuts a distal end face of the annular head such that the stopper portion defines a final insertion position of the barrel tip portion, and the tip of the puncture needle penetrates the bottom wall through the base end surface of the bottom wall such that the bottom wall seals the tip of the puncture needle,
   wherein a length from the base end surface of the bottom wall to a temporary stopper portion is longer than a length from the tip of the puncture needle to a distal end of the annular head, and
   wherein, when the barrel tip portion inserts from the open end of the cap into the receiving hole to attach the cap to the barrel tip portion, the temporary stopper portion is configured to abut against the annular head such that insertion of the barrel tip portion into the receiving hole is temporarily stopped and an axis of the receiving hole is substantially aligned with an axis of the puncture needle.
   wherein, when the annular head of the barrel tip portion is inserted further into the receiving hole beyond the temporary stopper portion, the temporary stopper portion deforms elastically to allow the annular head of the barrel tip portion to enter the first portion of the receiving hole.

16. A method of assembling a syringe assembly, the method comprising:
   providing a barrel assembly comprising:
      a cylindrical barrel body having an opening at a base end;
      a barrel tip portion having an annular head and being disposed at an end of the barrel body; and
      a puncture needle having a needle hole and being held in the barrel tip portion such that a tip of the puncture needle projects from the barrel tip portion; and
   providing a cap comprising:
      a closed bottom wall at a distal end of the cap,
      an open end portion at a proximal end of the cap,
      a side wall extending from the bottom wall toward the open end portion, and
      a cylindrical receiving hole formed by the bottom wall, the side wall, and the open end portion, the receiving hole being configured to receive at least part of the barrel tip portion and the puncture needle,
   wherein the bottom wall has a base end surface that faces the receiving hole, and
   wherein the receiving hole includes:
      a first portion having an inner diameter that is smaller than an outer diameter of the annular head;
      a stopper portion disposed at a distal end of the first portion;
      a second portion that extends from the stopper portion to said base end surface, an inner diameter of the second portion being smaller than the inner diameter of the first portion;
      a third portion disposed at a proximal end of the receiving hole; and
      a temporary stopper portion disposed between the third portion and the first portion and configured to deform elastically,
   wherein a minimum of the inner diameter of the second portion is twice or greater than an outer diameter of the puncture needle,
   wherein a length from the base end surface of the bottom wall to a temporary stopper portion is longer than a length from the tip of the puncture needle to a distal end of the annular head,
   inserting the puncture needle and the barrel tip portion of the barrel assembly from the open end portion into the receiving hole until the temporary stopper portion abuts against the annular head of the barrel tip portion and the tip of the puncture needle is disposed in the second portion of the receiving hole,
   aligning an axis of the receiving hole with an axis of the puncture needle by the abutting the temporary stopper portion and the annular head of the barrel tip portion,
   further inserting the barrel tip portion of the barrel assembly into the receiving hole until the stopper portion abuts against a distal end face of the annular head,
   wherein, when the further insertion of the barrel tip portion into the receiving hole, the temporary stopper portion deforms elastically to allow the annular head of the barrel tip portion to enter the first portion of the receiving hole, wherein, when the stopper portion abuts against an end face of the annular head, the first portion is in contact with an outer peripheral surface of the annular head, and the tip of the puncture needle penetrates the bottom wall through the base end surface of the bottom wall such that the bottom wall seals the tip of the puncture needle.

* * * * *